United States Patent [19]

Fabian et al.

[11] 4,022,796

[45] May 10, 1977

[54] 2,3-DIHYDRO-N-(5-METHYL-3-ISOX-AZOLYL)-3-OXO-1,2-BENZOTHIAZOLE-2-ACETAMIDE 1,1-DIOXIDE

[75] Inventors: Arthur C. Fabian, Flanders; Jerome D. Genzer, Livingston; Charles Francis Kasulanis, Hopatcong; John Shavel, Jr., Mendham; Harold Zinnes, Rockaway, all of N.J.

[73] Assignee: Warner-Lambert Company, Morris Plains, N.J.

[22] Filed: Dec. 29, 1975

[21] Appl. No.: 644,986

Related U.S. Application Data

[62] Division of Ser. No. 577,568, May 21, 1975, Pat. No. 3,957,772.

[52] U.S. Cl. .............................................. 260/301
[51] Int. Cl.$^2$ ..................................... C07D 275/06
[58] Field of Search ................................. 260/301

[56] References Cited

UNITED STATES PATENTS 3,957,772   5/1976   Fabian et al. ................. 260/243 R Primary Examiner—R. J. Gallagher
Attorney, Agent, or Firm—Albert H. Graddis; Frank S. Chow; Anne M. Kelly

[57] ABSTRACT

A novel process for preparing 4-hydroxy-3-(5-methyl-3-isoxazolylcarbamoyl)-2-methyl-2H-1,2-benzothiazine 1,1-dioxide (I), starting with 3-amino-5-methylisoxazole (II) is disclosed. Compound I exhibits anti-inflammatory properties and is useful for treating inflammation. In the process of the invention an intermediate obtained, 2,3-dihydro-N-(5-methyl-3-isoxazolyl)-3-oxo-1,2-benzisothiazole-2-actamide 1,1-dioxide (IV) undergoes rearrangement to provide 1-{[5-(4-hydroxy-2H-1,2-benzothiazin-3-yl)-1,2,4-oxadiazol-3-yl]methyl} ethanone, S,S-dioxide (V), which is methylated, according to conventional procedures. The methylated intermediate VI, upon further treatment, undergoes a second rearrangement to obtain the desired anti-inflammatory compound I.

1 Claim, No Drawings

2,3-DIHYDRO-N-(5-METHYL-3-ISOXAZOLYL)-3-OXO-1,2-BENZOTHIAZOLE-2-ACETAMIDE 1,1-DIOXIDE

This is a division, of application Ser. No. 577,568 filed May 21, 1975 now U.S Pat. No. 3,957,772 issued May 18, 1976.

BACKGROUND OF THE INVENTION

1. Field of the Invention

The present invention is concerned with a process for the production of 4-hydroxy-3-(5-methyl-3-isoxazolylcarbamoyl)-2-methyl-2H-1,2-benzothiazine 1,1-dioxide (IV) and to certain intermediates used in the production thereof.

2. Description of the Prior Art

As disclosed by Zinnes, Schwartz and Shavel, in U.S. Pat. No. 3,822,258, 4-hydroxy-3-(3-isoxazolylcarbamoyl)-2H-1,2-benzothiazine 1,1-dioxides exhibit anti-inflammatory activity. According to U.S. Pat. No. 3,822,258, these active compounds are prepared by reacting a 2-substituted-4-hydroxy-2H-1,2-benzothiazine-3-carboxylate 1,1-dioxide with a substituted 3-aminoisoxazole. Other synthetic routes for obtaining 4-hydroxy-3-(5-methyl-3-isoxazolylcarbamoyl)-2-methyl-2H-1,2-benzothiazine 1,1-dioxide have been disclosed by Lombardino in U.S. Pat. No. 3,853,862 and by Sircar, Zinnes and Shavel in U.S. Pat. No. 3,821,211. A key intermediate in the Lombardino process is N-aryl-N'-alkyl-N'-(2'-alkyoxycarbanoyl-benzenesulfonyl)-glycineamide. The Sircar et al. process describes the treatment of a pyrrolidine enamine of 3,4-dihydro-2-methyl-4-oxo-2H-1,2-benzothiazine 1,1-dioxide with phosgene and triethylamine, followed by the reaction of the compound obtained with 3-amino-5-methylisoxazole, and hydrolysis.

Related anti-inflammatory agents and processes for their preparation are described by Lombardino in U.s. Pat. No. 3,591,584 and by Rasmussen in U.S. Pat. No. 3,501,466. Lombardino et al., in J. Med. Chem. 14: 1171–1175 (1971) shows the preparation of 3-methoxycarbonyl-4-hydroxy-2H-1,2-benzothiazine 1,1-dioxide from 3-oxo-1,2-benzisothiazoline-2-acetic acid methyl ester. Zinnes et al. discuss a similar reaction starting with the analogous methyl ketone in J. Org. Chem. 30: 2241–2246 (1965).

Rearrangement reactions of substituted isoxazoles and oxadiazoles are discussed generally in H. C. Van Der Plas, *Ring Transformations of Heterocycles*, Volume 1, Chapter 3, 1973, Academic Press, London, N.Y.

SUMMARY OF THE INVENTION

A process for the production of the compound of the formula:

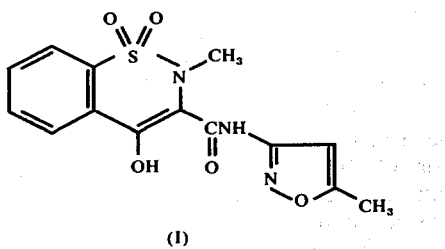

(I)

is described. 3-Amino-5-methylisoxazole (II) is reacted with a haloacetylhalide to obtain 3-(haloacetamido)-5-methylisoxazole (III) which is then reacted with an alkali metal salt of saccharin to form compound IV:

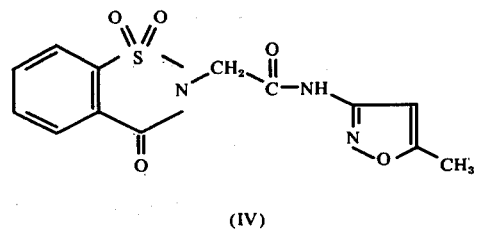

(IV)

Compound IV is treated with an alkali metal alkoxide in an inert solvent at a controlled temperature to form the benzothiazine-oxadiazole derivative V:

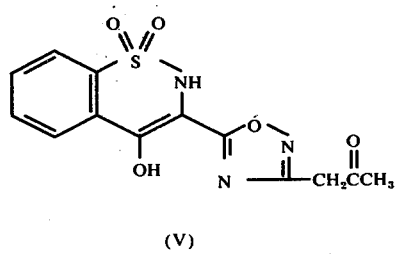

(V)

which is methylated on the sulfonamide nitrogen by conventional procedures, at controlled temperatures, to yield the corresponding methylated compound VI. Compound VI is then transformed into the desired compound I by heating with a base. Alternatively, compound V may be rearranged and methylated in a one-step reaction by heating with a methylating agent in a solvent/base system.

DESCRIPTION OF THE PARTICULAR EMBODIMENTS

According to the present invention, a novel process for the production of 4-hydroxy-3-(5-methyl-3-isoxazolylcarbamoyl)-2-methyl-2H-1,2-benzothiazine 1,1-dioxide (I):

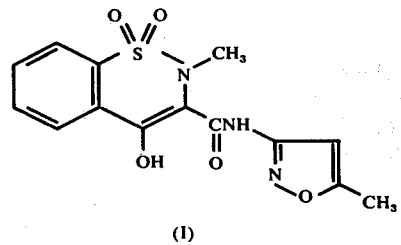

(I)

is initiated by reacting compound II:

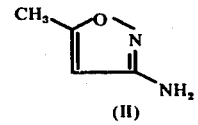

(II)

3-Amino-5-methylisoxazole with haloacetylhalide, such as chloroacetylchloride in an inert solvent, such as chloroform, containing excess organic base, preferably pyridine. After stirring the reaction mixture for several hours, compound III is obtained:

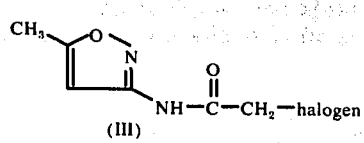

3-(Haloacetamido)-5-methylisoxazole which is then condensed with an alkali metal salt of saccharin, preferably sodium saccharin, in an inert solvent, such as N,N'-dimethylformamide (DMF). Reactants are used in approximately equimolar quantities and the condensation reaction may be conducted for example, at about 100° C. for about 3 hours, to yield compound IV:

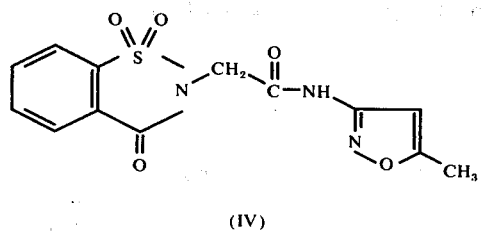

2,3-Dihydro-N-(5-methyl-3-isoxazolyl)-3-oxo-1,2-benzisothiazole-2-acetamide 1,1-dioxide Rearrangement of IV is effected using an alkali metal alkoxide of a lower alcohol, such as sodium methoxide, in an inert solvent at a controlled temperature. Typically, more than three moles, preferably about four moles of sodium methoxide per mole of IV in dimethylformamide at a preferred temperature of from about 60° C. to about 70° C. is used for the rearrangement. After acidification with a mineral acid, for example HCl, compound V is obtained:

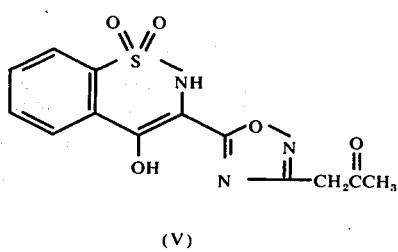

1-{[5-(4-Hydroxy-2H-1,2-benzothiazin-3-yl)-1,2,4-oxadiazol-3-yl]methyl}ethanone S,S-dioxide The success of this dual rearrangement is dependent on the reaction temperature, since lower or higher temperatures have been found to yield unsatisfactory results.

Conversion of V to compound VI is effected by conventional methylation procedures using standard methylating agents such as methyl iodide and/or dimethylsulfate in aqueous inert solvents such as the lower alcohols, containing excess base. The reaction temperature is controlled preferably, between 10°–25° C., as higher temperatures do not afford compound VI, as is more fully exemplified below. Typically, an excess, preferably two equivalents of aqueous sodium hydroxide are employed with Proprietary Solvent No. III (SOLOX) with an excess, preferably 1.5 equivalents of dimethylsulfate. SOLOX, which is sold commercially by U.S. Industrial Chemical Co., New York, N.Y., is a general-purpose solvent formulation comprised of specially denatured alcohol with low percentages of solvent modifiers. Stirring the above reaction mixture for about three hours, at temperatures ranging between about 10° to 25° C., afforded, after acidification with a mineral acid, compound VI:

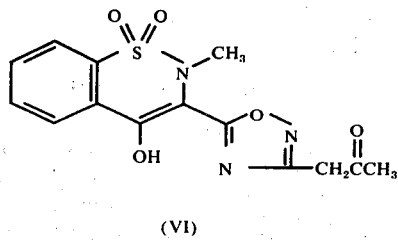

1-{[5-(4-Hydroxy-2-methyl-2H-1,2-benzothiazin-3-yl)-1,2,4-oxadiazol-3-yl]methyl}ethanone S,S-dioxide Transformation of VI to the title compound I is effected by heating (> 100° C.) in an inert solvent, such as xylene, containing an organic base, preferably triethylamine. Heating VI (90°–100° C.) in an aqueous base such as sodium hydroxide also affords I after acidification.

Alternatively, compound V may be converted to compound I using conventional methylating agents in aqueous alcohols containing an excess of base at elevated temperatures. For example, compound V is placed in SOLOX containing an excess, preferably 3.5 equivalents of aqueous sodium hydroxide, with an excess, preferably 1.5 equivalents of dimethylsulfate, and heated at reflux (about 75° to 80° C.) for about one and one half hours. After acidification, compound I is obtained.

Direct conversion of compound V to compound I is also effected in a non-aqueous medium, such as dimethylformamide, at elevated temperatures (about 50° to 80° C., preferably 60° C.), using an excess, preferably two equivalents of a metal hydride base, preferably sodium hydride, followed by the addition of a conventional methylating agent, such as methyl iodide. Acidification affords compound I.

The corresponding alkali metal, alkaline earth metal and amine salts of final compound I may be prepared by treating compound I with the desired base, e.g., sodium alkoxide, potassium alkoxide, sodium hydroxide, potassium hydroxide, calcium hydroxide, pyrrolidine and the like according to conventional procedures. If desired, the alkali metal salt of compound I may be obtained directly in certain of the procedures of this invention by omission of the acidification reaction in the final process step.

The starting material 2-amino-5-methylisoxazole (II) used in the process of this invention is known and may be prepared as described in Netherlands Pat. No. 6,511,924. Compound II is commercially available from Hoffmann La Roche, Nutley, New Jersey.

The final compound (I) prepared according to the process of this invention, is described in U.S. Pat. No. 3,816,628, as having useful anti-inflammatory, antipyretic and analgesic properties. When administered orally to rats at a dose of 10–200 mg/kg, it is able to cause reduction in swelling of the paw induced by injection into the foot pads of an irritant such as carrageenin. Therapeutically or prophylactically administered orally at a dose of 15–200 mg/kg, the compound inhibits adjuvant induced polyarthritis in the rat. Oral doses of 25–100 mg/kg are sufficient to inhibit yeast induced hyperthermia in the rat. At oral doses of 25–200 mg/kg it exhibits a significant analgesic effect as determined by the phenylquinone writhing procedure in mice.

Generally speaking, compound I is indicated in conditions such as pain resulting from arthritis, bursitis, and the like. A daily dosage regimen of about 0.5 grams to about 2 grams in several divided doses is recommended for a mammal weight about 70 kg body weight to relieve the pain and swelling associated with these conditions. Compound IV may be administered either orally or by injection.

In order to use compound I, it is formulated into dosage forms such as tablets or syrups by blending with an inert pharmaceutical carrier such as lactose or simple syrup by methods well known to the pharmacists art. For injectionable dosage forms, it is formulated with vehicles such as water, peanut oil, sesame oil, and the like. In these dosage forms, the active ingredient is from about 0.5 grams to 1 grams per dosage unit.

The following definitions apply to all of the compounds and reaction procedures of this invention, as well as to reagents and intermediates used in the preparation thereof: halogen is meant to include chlorine, bromine and iodine; the term alkali metal is meant to include sodium, potassium and the like; the term lower alcohol is meant to include 1 to 5 carbon, straight or branched chain alcohols; the term base is meant to include those bases commonly used in an aqueous reaction medium, such as sodium hydroxide, potassium hydroxide and the like; the term organic base is meant to include those bases commonly used in a non-aqueous reaction medium, such as pyridine, diethylamine, triethylamine, and the like; the term metal hydride base is meant to include alkali metal and alkaline earth metal hydrides such as sodium hydride, potassium hydride, calcium hydride and the like.

In order to further illustrate this invention, the following examples are provided:

EXAMPLE 1

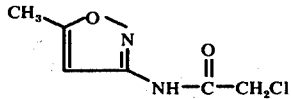

3-(Chloroacetamido)-5-Methylisoxazole

To 800 ml of chloroform is added 118 grams (1.12 moles) of 3-amino-5-methylisoxazole followed by 118 grams (1.5 moles) of pyridine. To this solution is added 147 grams (1.3 moles) of chloroacetylchloride with the addition temperature maintained at 0°–10° C. The reaction is then stirred at room temperature for 1 hour, filtered and dried in a vacuum desiccator to give 116 grams (56%) of 3-(chloroacetamido)-5-methylisoxazole, mp 192°–195° C. This material is slightly irritating to the skin and due caution should be exercised.

Analysis: Calc'd for $C_6H_7ClN_2O_2$ (174.58): C, 41.28; H, 4.40; N, 16.05; Cl, 20.31. Found: C, 41.55; H, 4.10; N, 15.79; Cl, 20.50.

EXAMPLE 2

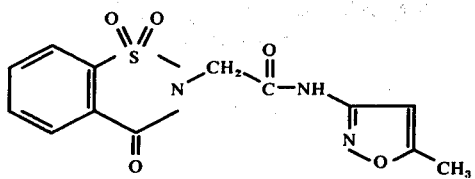

(IV)

2,3-Dihydro-N-(5-Methyl-3-Isoxazolyl)-3-Oxo-1,2-Benzisothiazole-2-Acetamide 1,1-Dioxide (IV)

To 2.31 liters of DMF is added 479 grams (2.75 moles) of 3-(chloroacetamino)-5-methylisoxazole followed by 699 grams (2.9 moles) of sodium saccharin dihydrate. The mixture is heated to 100° C. and this temperature is maintained for 2 hours. The cooled reaction mixture is poured into 8 liters of water, filtered and the wet cake is recrystallized from 15 liters of ethanol to give 658 grams (74.8%) of 2,3,dihydro-N-(5-methyl-3-isoxazolyl)-3-oxo-1,2-benzisothiazole-2-acetamide 1,1-dioxide, mp 218°–220° C.; I.R. and NMR spectra are consistant with the structure.

Analysis: Calc'd for $C_{13}H_{11}N_3O_5S$ (321.30), C, 48.60; H, 3.45; N, 13.08; S, 9.98. Found: C, 48.62; H, 3.61; N, 13.28; S, 10.19.

EXAMPLE 3

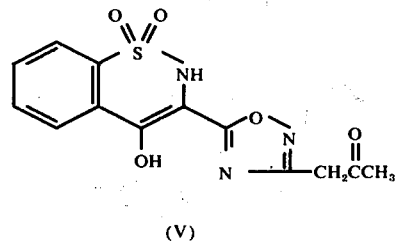

(V)

1-{[5-(4-Hydroxy-2H-1,2-Benzothiazin-3-yl)-1,2,4-Oxadiazol-3-yl]Methyl}Ethanone S,S-Dioxide (V)

To 300 ml DMF is added 67.5 grams (1.25 moles) of sodium methoxide. This is heated to 55° C. whereupon a solution of 100 grams (0.31 moles) of 2,3-dihydro-N-(5-methyl-3-isoxazolyl)-3-oxo-1,2-benzisothiazole-2-acetamide 1,1-dioxide in 350 ml of DMF is added. The temperature is maintained at 60°–70° C. for a half hour and poured into aqueous acid. This afforded 71 grams (71%) of crude product V.

Purification is achieved by a hot aqueous methanol treatment, and this afforded 1-{[5-(4-hydroxy-2H-1,2-benzothiazin-3-yl)-1,2,4-oxadiazol-3-yl]methyl}ethanone S,S-dioxide, mp 187°–189° C.; IR and NMR are consistent with the structure.

Analysis: Calc'd for $C_{13}H_{11}N_3O_5S$ (321.30), C, 48.60; H, 3.45; N, 13.08; S, 9.98. Found: C, 48.55; H, 3.49; N, 12.93; S, 10.16.

EXAMPLE 4

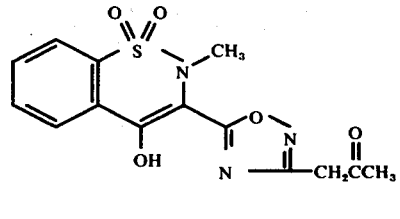

(VI)

1-{[5-(4-Hydroxy-2-Methyl-2H-1,2-Benzothiazin-3-yl)-1,2,4-Oxadiazol-3-yl]Methyl}Ethanone S,S-Dioxide (VI)

To 160 ml of 56% aqueous proprietary solvent No. 3 (SOLOX) is added 3.21 grams (0.01 mole) of{1- [5-(4-hydroxy-2H-1,2-benzothiazin-3-yl)-1,2,4-oxadiazol-3-yl]-methyl ethanone}S,S-dioxide and the mixture is cooled to 5° C., whereupon 20 ml of 1 N NaOH is added dropwise, the temperature being maintained below 10° C. To this is added 1.8 grams (0.015 mole) of dimethylsulfate and the reaction mixture is stirred for 3 hours, maximum temperature 25° C. Acidification with 6 N HCl afforded 2.8 grams (85%) of analytical 1-{[5-(4-hydroxy-2-methyl-2H-1,2-benzothiazin-3-yl)-1,2,4-oxadiazol-3-yl]methyl}ethanone S,S-dioxide, mp 143°–145° C.; IR and NMR are consistant with the structure.

Analysis: Calc'd for $C_{14}H_{13}N_3O_5S$ (335.32) C, 50.15; H, 3.91; N, 12.53; S, 9.56. Found: C, 49.97; H, 3.98; N, 12.52; S, 9.72.

EXAMPLE 5

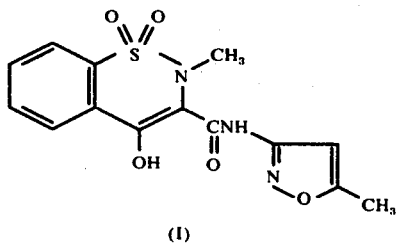

(I)

4-Hydroxy-3-(5-Methyl-3-Isoxazolylcarbamoyl)-2-Methyl-2H-1,2-Benzothiazine 1,1-Dioxide (I)

To 80 ml xylene is added 4.0 grams (0.012 mole) of 1-{[5-(4-hydroxy-2-methyl-2H-1,2-benzothiazin-3-yl)-1,2,4-oxadiazol-3-yl]methyl}ethanone S,S-dioxide followed by 0.4 grams (0.0046 mole) of triethylamine and the temperature is brought to 115°–120° C. for 30 minutes. The reaction mixture is cooled and filtered to afford 3.6 grams (90%) of 4hydroxy-3-(5-methyl-3-isoxazolylcarbomoyl)-2-methyl-2H-1,2-benzothiazine 1,1-dioxide, mp 252°–254° C.

Analysis: Calc'd for $C_{14}H_{13}N_3O_5S$ (335.32) C, 50.15; H, 3.91; N, 12.53; S, 9.56. Found: C, 49.96; H, 3.95; N, 12.47; S, 9.58.

EXAMPLE 6

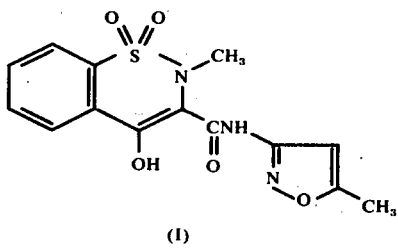

(I)

4-Hydroxy-3-(5-Methyl-3-Isoxazolylcarbamoyl)-2-Methyl-2H-1,2-Benzothiazine 1,1-Dioxide (I)

To 20 ml DMF is added 3.2 grams (10 mmol) of the unalkylated oxadiazole, 1-{[5-(4-hydroxy-2H-1,2-benzothiazin-3yl)-1,2,4-oxadiazol-3-yl]methyl}ethanone S,S-dioxide. To this is added 0.9 grams of 57% NaH (21.4 mmol) and the temperature rises to 60° C. The temperature is allowed to cool naturally to 25° C., whereupon 1.4 grams (10 mmol) of methyl iodide dissolved in 1 ml of DMF is added. The reaction is heated (60° C.) for 2 hours, cooled and acidified to give 2.3 grams (70%) of a material whose thin layer chromatography matched that of 4-hydroxy-3-(5-methyl-3-isoxazolylcarbamoyl)-2-methyl-2H-1,2-benzothiazine 1,1-dioxide of Example 5.

EXAMPLE 7

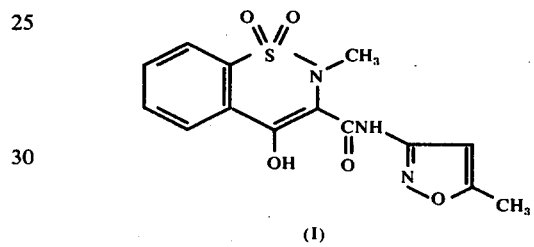

(I)

4-Hydroxy-3-(5-Methyl-3-Isoxazolylcarbamoyl)-2-Methyl-2H-1,2-Benzothiazine 1,1-Dioxide (I)

To 60 ml SOLOX is added 3.21 grams (0.01 mole) of 1-{[5-(4-hydroxy-2H-1,2-benzothiazin-3-yl)-1,2,4-oxadiazol-3-yl]methyl}ethanone S,S-dioxide followed by 35 ml of 1 N NaOH. To this is added 1.89 grams (0.015 mole) of dimethylsulfate and the reaction is heated to reflux (75°–80° C.) for one and a half hours. Cooling and filtration afforded 2.3 grams (70%) of crude product I. Purification (DMF/SOLOX recrystallization) gave 4-hydroxy-3-(5-methyl-3-isoxazolylcarbamoyl)-2-methyl-2H-1,2-benzothiazine 1,1-dioxide, mp 247°–250° C., dec. whose thin layer chromatography is identical to the material prepared directly from 1-{[5-(4-hydroxy-2-methyl-2H-1,2-benzothiazin-3-yl)-1,2,4-oxadiazol-3-yl]methyl}ethanone S,S-dioxide in Example 5.

We claim:

1. 2,3-Dihydro-N-(5-methyl-3-isoxazolyl)-3-oxo-1,2-benzisothiazole-2-acetamide 1,1-dioxide.

* * * * *